United States Patent
Chen et al.

(10) Patent No.: US 11,649,239 B2
(45) Date of Patent: May 16, 2023

(54) CRYSTAL FORM A OF (5-AMINO-8-(2-METHYL-6-(TRIFLUOROMETHYL)PYRIDIN-4-YL)-7-PHENYL-[1,2,4]TRIAZOLO[1,5-C]PYRIMIDIN-2-YL)METHANOL (COMPOUND 1)

(71) Applicant: Medshine Discovery Inc., Jiangsu (CN)

(72) Inventors: Kevin X. Chen, Shanghai (CN); Yanxin Yu, Shanghai (CN); Xinde Chen, Shanghai (CN); Li Zhang, Shanghai (CN); Zhaoguo Chen, Shanghai (CN); Cheng Xie, Shanghai (CN)

(73) Assignee: Medshine Discovery Inc., Jiangsu (CN)

( * ) Notice: Subject to any disclaimer, the term of this patent is extended or adjusted under 35 U.S.C. 154(b) by 290 days.

(21) Appl. No.: 17/044,127

(22) PCT Filed: Apr. 28, 2019

(86) PCT No.: PCT/CN2019/084822
§ 371 (c)(1),
(2) Date: Sep. 30, 2020

(87) PCT Pub. No.: WO2019/206336
PCT Pub. Date: Oct. 31, 2019

(65) Prior Publication Data
US 2021/0094957 A1    Apr. 1, 2021

(30) Foreign Application Priority Data
Apr. 28, 2018  (CN) .......................... 201810399876.6

(51) Int. Cl.
*C07D 487/04*  (2006.01)
(52) U.S. Cl.
CPC ........ *C07D 487/04* (2013.01); *C07B 2200/13* (2013.01)
(58) Field of Classification Search
CPC .................................................... C07D 487/04
USPC ......................................................... 544/263
See application file for complete search history.

(56) References Cited

U.S. PATENT DOCUMENTS

| 6,222,035 B1 | 4/2001 | Tsumuki et al. |
| 7,041,666 B2 | 5/2006 | Matasi et al. |
| 2020/0131184 A1 | 4/2020 | Chen et al. |

FOREIGN PATENT DOCUMENTS

| WO | WO 03/048164 A2 | 6/2003 | |
| WO | WO-2019206336 A1 * | 10/2019 | ............... A61P 25/16 |

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — McDermott Will & Emery LLP

(57) ABSTRACT

Disclosed in the present invention are a crystal form of a [1,2,4]triazolo[1,5-c]pyrimidine compound and a preparation method thereof. Further disclosed is a use of the crystal form in the preparation of a medicament for treating $A_{2A}$ receptor related diseases.

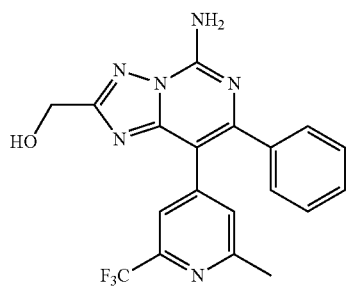

(I)

12 Claims, 2 Drawing Sheets

CRYSTAL FORM A OF (5-AMINO-8-(2-METHYL-6-(TRIFLUOROMETHYL)PYRIDIN-4-YL)-7-PHENYL-[1,2,4]TRIAZOLO[1,5-C]PYRIMIDIN-2-YL)METHANOL (COMPOUND 1)

CROSS-REFERENCE TO RELATED APPLICATIONS

The present application is a United States National Phase under 35 U.S.C. § 371 of International Application No. PCT/CN2019/084822, filed on Apr. 28, 2019, which claims priority to, and the benefit of Chinese Patent Application No. CN201810399876.6, filed on Apr. 28, 2018, the entire contents of each of which are incorporated by reference herein.

FIELD OF THE INVENTION

The present disclosure relates to a crystal form of [1,2,4]triazolo[1,5-c]pyrimidine compound, a preparation method thereof, and also a use of the crystal form in the preparation of a medicament for the treatment of diseases related to the $A_{2A}$ receptor.

BACKGROUND OF THE INVENTION

Adenosine $A_{2A}$ receptor is widely distributed in human tissues. The receptor is highly expressed in tissues and organs such as spleen, thymus, white blood cells, platelets, GABAergic neurons and olfactory bulb. It is also expressed in other parts such as heart, lung, blood vessel and brain. Adenosine $A_{2A}$ receptor generally co-exists with and binds to other GPCRs to form heterodimers. For example, the $A_{2A}$ receptor can form heterodimers with dopamine $D_2$, cannabinoid $CB_1$, glutamate mGluR5, etc. Adenosine $A_{2A}$ receptor plays an important role in life activities such as regulating vasodilation, supporting the formation of new blood vessels, and protecting body tissues from the damage caused by inflammation. Adenosine $A_{2A}$ receptor also affects the activity of indirect pathways in the basal ganglia.

In solid tumors, the decomposition of cell tissue and the hypoxic environment cause the decomposition of a large amount of ATP, resulting in extracellular enrichment of adenosine to an abnormally high concentration, which is 10 to 20 times the normal value. Binding of the high concentration of adenosine to the $A_{2A}$ receptor may activate the adenosine signaling pathway, which is a mechanism that protects body tissues through immunosuppression when the body tissues are damaged. The activation of the adenosine signaling pathway leads to a long-term suppression of the innate immune response, which may produce immune tolerance, and in turn lead to uncontrolled growth of malignant tumors. The binding of adenosine to the $A_{2A}$ receptor in white blood cells (such as lymphocytes, T lymphocytes, natural killer cells, dendritic cells, etc.) inhibits the effector functions of these white blood cells in the immune system. The binding of adenosine to the $A_{2A}$ receptor increases the expression of CD39, CD73 and CTLA4 (T cell checkpoints), thereby generating more $T_{reg}$ cells with stronger immunosuppressive properties. Blocking the adenosine signaling pathway of the $A_{2A}$ receptor may reduce the inhibitory effect on the immune system and enhance the immune function of T cells. Therefore, it is considered to be a promising negative feedback mechanism that can inhibit the tumor growth.

SUMMARY OF THE INVENTION

The present disclosure provides a crystal form A of compound 1, wherein the X-ray powder diffraction pattern thereof has characteristic diffraction peaks at the following 2θ angles: 11.30±0.2°, 16.90±0.2°, and 22.52±0.2°.

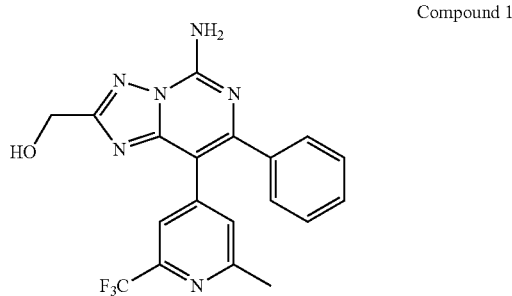 [SMILES: Cc1cc(-c2c(-c3ccccc3)nc(N)n3nc(CO)nc23)cc(C(F)(F)F)n1]

Compound 1

In some embodiments of the present disclosure, provided herein is the crystal form A of compound 1, wherein the X-ray powder diffraction pattern thereof has characteristic diffraction peaks at the following 2θ angles: 8.08±0.2°, 11.30±0.2°, 14.00±0.2°, 16.90±0.2°, 18.30±0.2°, 22.52±0.2°, 23.15±0.2°, and 25.26±0.2°.

In some embodiments of the present disclosure, provided herein is the crystal form A of compound 1, wherein the XRPD pattern thereof is shown in FIG. 1.

In some embodiments of the present disclosure, provided herein is the crystal form A of compound 1, wherein the analytical data of the XRPD pattern thereof is shown in Table 1.

TABLE 1

Analytical data of the XRPD pattern of the crystal form A of compound 1

| No. | 2θ Angle (°) | D-spacing (Å) | Height | Relative height (%) | Area | Relative area (%) |
| --- | --- | --- | --- | --- | --- | --- |
| 1 | 7.074 | 12.4848 | 633 | 9.5 | 8601 | 9.2 |
| 2 | 8.083 | 10.9295 | 1176 | 17.6 | 15789 | 16.9 |
| 3 | 11.298 | 7.8255 | 3714 | 55.6 | 54248 | 58.1 |
| 4 | 13.999 | 6.3208 | 959 | 14.4 | 12297 | 13.2 |
| 5 | 15.105 | 5.8604 | 274 | 4.1 | 3813 | 4.1 |
| 6 | 16.899 | 5.2422 | 2842 | 42.6 | 46090 | 49.3 |
| 7 | 18.3 | 4.8439 | 2413 | 36.1 | 36735 | 39.3 |
| 8 | 20.706 | 4.2863 | 573 | 8.6 | 9673 | 10.4 |
| 9 | 22.523 | 3.9444 | 6677 | 100 | 93430 | 100 |
| 10 | 23.152 | 3.8386 | 2449 | 36.7 | 30428 | 32.6 |
| 11 | 24.237 | 3.6692 | 229 | 3.4 | 3955 | 4.2 |
| 12 | 24.472 | 3.6344 | 302 | 4.5 | 5640 | 6 |
| 13 | 25.264 | 3.5223 | 921 | 13.8 | 10799 | 11.6 |
| 14 | 25.992 | 3.4252 | 326 | 4.9 | 5303 | 5.7 |
| 15 | 26.562 | 3.353 | 509 | 7.6 | 6889 | 7.4 |
| 16 | 28.082 | 3.1749 | 792 | 11.9 | 11609 | 12.4 |
| 17 | 29.444 | 3.031 | 585 | 8.8 | 8449 | 9 |
| 18 | 31.456 | 2.8416 | 740 | 11.1 | 10490 | 11.2 |
| 19 | 33.982 | 2.636 | 270 | 4 | 3506 | 3.8 |
| 20 | 36.702 | 2.4466 | 101 | 1.5 | 2852 | 3.1 |
| 21 | 36.959 | 2.4301 | 110 | 1.6 | 2843 | 3 |
| 22 | 38.043 | 2.3634 | 314 | 4.7 | 4575 | 4.9 |

In some embodiments of the present disclosure, provided herein is the crystal form A of compound 1, wherein the differential scanning calorimetry (DSC) curve thereof has a starting point of the endothermic peak at 198.61±2° C.

In some embodiments of the present disclosure, provided herein is the crystal form A of compound 1, wherein the DSC curve thereof is shown in FIG. 2.

In some embodiments of the present disclosure, provided herein is the crystal form A of compound 1, wherein the thermogravimetric analysis (TGA) curve thereof has a weight loss of up to 0.4423% at 199.80±3° C.

In some embodiments of the present disclosure, provided herein is the crystal form A of compound 1, wherein the TGA curve thereof is shown in FIG. 3.

The present disclosure also provides a use of the crystal form A of compound 1 in the preparation of a medicament for the treatment of diseases related to the $A_{2A}$ receptor.

Technical Effects

The crystal form A of compound 1 has stable properties, low hygroscopicity, and good prospect of druggability. The crystal form A of compound 1 disclosed herein has good stability and druggability, and it has a significant inhibitory effect on the adenosine signaling pathway activated by the binding of high concentration of adenosine to the $A_{2A}$ receptor in the tumor microenvironment. According to the model colorectal cancer in CT-26 mice, it was found that the crystal form A of compound 1 had a significant inhibitory effect on the tumor.

DEFINITION AND DESCRIPTION

Unless otherwise stated, the following terms and phrases used herein are intended to have the following meanings. A specific phrase or term should not be considered uncertain or unclear without a specific definition, but should be understood in the ordinary sense. When a trade name appears herein, it is intended to refer to the corresponding commodity or the active ingredient thereof.

The intermediate compounds of the present disclosure can be prepared by a variety of synthetic methods well known to those skilled in the art, including the specific embodiments listed below, the embodiments formed by combining them with other chemical synthetic methods, and the equivalent alternative methods well known to those skilled in the art. The preferred embodiments include, but are not limited to, the examples of the present disclosure.

The chemical reactions in the specific embodiments disclosed herein are completed in a suitable solvent, which must be suitable for the chemical changes of the present disclosure and the reagents and materials required. In order to obtain the compound of the present disclosure, it is sometimes necessary for those skilled in the art to modify or select synthetic steps or reaction schemes based on the existing embodiments.

The present disclosure will be described in detail below through examples, which are not intended to limit the present disclosure.

All solvents used in the present disclosure are commercially available and can be used without further purification.

The present disclosure uses the following abbreviations: DMF stands for dimethylformamide; Pd(PPh$_3$)$_4$ stands for tetrakis(triphenylphosphino)palladium(0); EtOH stands for ethanol; NaOH stands for sodium hydroxide; and MTBE stands for methyl tert-butyl ether.

The compounds are named manually or ChemDraw® software, and the commercially available compounds use the supplier catalog names.

X-Ray Powder Diffraction (XRPD) Method Used in the Present Disclosure

About 10 to 20 mg of sample was used for XRPD analysis.

The detailed XRPD parameters were as follows:
Light tube: Cu, kα, (λ=1.54056 Å).
Voltage of the light tube: 40 kV, current of the light tube: 40 mA
Divergence slit: 0.60 mm
Detector slit: 10.50 mm
Anti-scatter slit: 7.10 mm
Scanning range: 3 or 4 to 40 deg
Step size: 0.02 deg
Step length: 0.12 seconds
Rotation speed of sample disk: 15 rpm Differential Scanning Calorimetry (DSC) Method Used in the Present Disclosure The sample (0.5 to 1 mg) was taken and put into the DSC aluminum pan for testing. The method was that: the sample was heated from 25° C. to 300° C. or 350° C. at a heating rate of 10° C./min.

Thermogravimetric Analysis (TGA) Method Used in the Present Disclosure

The sample (2 to 5 mg) was taken and put into a TGA platinum pot for testing. Under the condition of 25 mL/min N$_2$, the sample was heated from room temperature to 300° C. or 20% weight loss at a heating rate of 10° C./min.

DETAILED DESCRIPTION OF THE INVENTION

Figure 1:
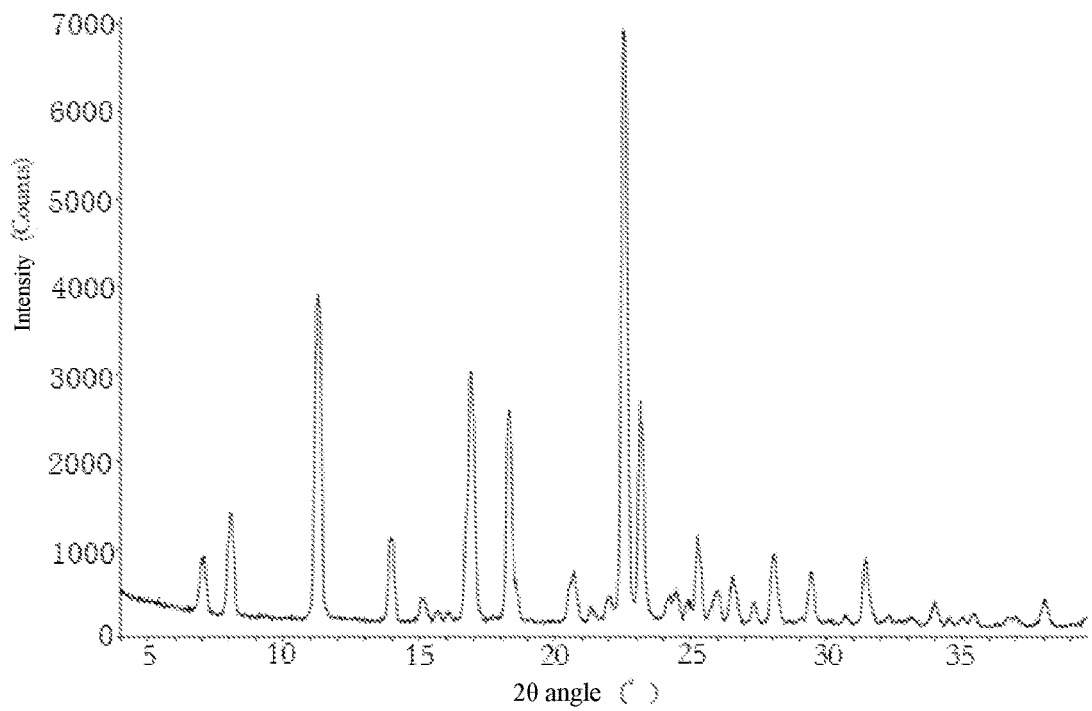
FIG. 1 is the XRPD pattern of the crystal form A of compound 1 using Cu-Kα radiation.

In order to better understand the content of the present disclosure, the present disclosure is further illustrated below in conjunction with specific examples, but the specific embodiments are not intended to limit the content of the present disclosure.

Step 1:

Anhydrous tetrahydrofuran (24 L) was added to a 50 L high and high-low temperature jacketed reaction kettle. Compound a (2464.84 g, 13.58 mol, 1 eq) was weighed and added to the reaction kettle in batches. Under the protection of nitrogen flow, the refrigeration was turned on, and the temperature of the reaction system was reduced to 0° C. The pressure was reduced by vacuum. A solution of methylmagnesium chloride in tetrahydrofuran (6.79 L, 20.37 mol, 3.0 M, 1.50 eq) was added into a 1 L constant pressure dropping funnel, and was slowly added dropwise into the reaction kettle under the protection of nitrogen. During the dropwise addition, the internal temperature of the reaction solution was controlled between 0 and 5° C. Pd(PPh$_3$)$_4$ (315.25 g, 271.54 mmol, 0.02 eq) was weighed and added to the reaction kettle in batches. Under the protection of nitrogen, the heating was turned on, and the reaction solution was heated to 70±5° C., and reacted for 16 hours with stirring. HPLC and LCMS showed that the reaction was completed. The reaction solution was cooled to room temperature, and slowly poured into 1500 mL of ice water. Then 200 g of ammonium chloride was added to the ice water, and the resulting mixture was stirred for 30 minutes and filtered. The filtrate was concentrated under reduced pressure to remove most of the solvent. A water pump was used to reduce the pressure, and the product was subjected to a reduced pressure distillation (110° C.) to give the compound b (1832.91 g, yield: 69.48%) as a yellow liquid.

LCMS (5-95AB): m/z: 162.1 [M+1].

$^1$H NMR (400 MHz, CDCl$_3$): δ 7.73 (t, J=7.6 Hz, 1H), 7.48-7.46 (d, J=8.0 Hz, 1H), 7.33-7.31 (d, J=8.0 Hz, 1H), 2.62 (s, 3H).

Step 2:

MTBE (4000 mL) was added to a 5 L reaction flask, and bis(pinacolato)diboron (385.81 g, 1.52 mol, 0.6 eq) was weighed and added to the reaction flask. 4,4'-Di-tert-butyl-2,2'-bipyridine (6.73 g, 25.07 mmol, 0.01 eq) and bis(1,5-cyclooctadiene)di-μ-methoxydiiridium(I) (6.73 g, 10.15 mmol, 0.004 eq) were weighed and added to the reaction flask. The air in the reaction flask was purged with nitrogen, and the reaction solution was stirred at 70±5° C. for 0.5 hours. Compound b (408.00 g, 2.53 mol, 1 eq) was slowly added to the reaction flask through a 1 L constant pressure dropping funnel. After the addition, the air in the reaction flask was purged with nitrogen again. The reaction solution was reacted with stirring at 70±5° C. for 16 hours. HPLC and LCMS showed that the reaction was completed. The reaction solution was cooled to room temperature, and concentrated under reduced pressure to remove the solvent. The residue was dissolved with a mixture of n-heptane and ethyl acetate (n-heptane:ethyl acetate=10:1, 3 L). The resulting mixture was poured into a chromatography column filled with silica gel (100 to 200 mesh, 2.5 Kg), and filtered with suction under reduced pressure. The silica gel filter cake was washed with ethyl acetate, and the filtrate was concentrated under reduced pressure to give the compound c (567.11 g, yield: 78.01%) as a white solid.

LCMS (5-95AB): m/z: 288.2 [M+1].

$^1$H NMR (400 MHz, CDCl$_3$): δ 7.83 (s, 1H), 7.70 (s, 1H), 2.65 (s, 3H), 1.37 (s, 12H).

Example 2: Preparation of Compound 1 and Crystal Form A Thereof

Step 1:

Methanol (30 L) was added to a 50 L reaction kettle, to which compound d (3300.08 g, 20.12 mol, 1.0 eq) was then added at 35° C. The solid on the surrounding wall of the reaction kettle was then rinsed with methanol (3 L). Hydrazine hydrate (2.99 L, 60.37 mol, 3.0 eq) with 98% purity was added, and the reaction system was stirred at 35° C. for 22.55 hours. LCMS and HPLC showed that the reaction was completed. The reaction solution was filtered, and the filter cake was collected and dried to give the compound e (3402.84 g, crude product) as a yellow solid.

LCMS (5-95AB): m/z: 160.1 [M+1].

$^1$HNMR (400 MHz, DMSO-d6): δ 8.13 (br s, 1H), 6.35 (br s, 2H), 5.96 (s, 1H), 4.24 (br s, 2H).

Step 2:

Benzyloxyacetic acid (1.97 L, 13.74 mol, 1.02 eq) was added to a 50 L reaction kettle, to which tetrahydrofuran (6 L) was then added. Then N,N-carbonyldiimidazole (2230.00 g, 13.74 mol, 1.02 eq) was slowly added in batches, and bubbles were generated at this time. The reaction kettle was kept open to the atmosphere, and tetrahydrofuran (3 L) was added. The resulting mixture was stirred at 19° C. for 3.17 hours. Compound e (2150.00 g, 13.47 mol, 1 eq) was slowly added in batches while the temperature was kept at 30° C., and finally the compound on the surrounding wall was rinsed with tetrahydrofuran (1.75 L). The reaction solution was stirred at 15 to 16° C. for 19.78 hours. LCMS and HPLC showed that the reaction was almost completed. The reaction solution was concentrated to dryness, and a prepared solution of citric acid in water (300 g citric acid dissolved in 8 L water) was added. The resulting mixture was stirred at 16° C. and filtered. The filter cake was slurried with methanol (10 L), and then filtered. The filter cake was collected and dried to give the compound f (2876.00 g, yield: 69.37%) as a yellow solid.

LCMS (5-95AB): m/z: 308.2 [M+1].

$^1$H NMR (400 MHz, d4-MeOH): δ 7.47-7.27 (m, 5H), 5.96 (s, 1H), 4.67 (s, 2H), 4.12 (s, 2H).

Step 3:

At 20° C., hexamethyldisilazane (18.9 L, 90.09 mol, 13.21 eq) and N,O-bis(trimethylsilyl)acetamide (16.8 L, 67.93 mol, 9.96 eq) were added to a 50 L reaction kettle. Then compound f (2100.00 g, 6.82 mol, 1 eq) was added, and the reaction solution was stirred at 120° C. for 22.77 hours. LCMS and HPLC showed that the reaction was completed. The reaction solution was cooled to 20° C., the stirring was turned off, and then the reaction solution was discharged. The discharged reaction solution was slowly added to a mixed solution of water (16.8 L) and methanol (16.8 L) in the reaction kettle in batches while the internal temperature was kept at 15 to 25° C. With the quenching progressed, a yellow solid was generated. The resulting mixture was filtered, and the filter cake was collected and dried to give the compound g (1480.72 g, yield: 74.90%) as a yellow solid.

LCMS (5-95AB): m/z: 290.0 [M+1].

$^1$H NMR (400 MHz, DMSO-d6): δ 8.38 (br s, 2H), 7.43-7.23 (m, 5H), 7.03 (s, 1H), 4.68 (s, 2H), 4.61 (s, 2H).

Step 4:

Compound g (1080.00 g, 3.73 mol, 1.0 eq) was added to 1,4-dioxane (10.8 L) and water (2.16 L), and then phenylboronic acid (350.78 g, 2.88 mol, 1.05 eq) and potassium carbonate (757.34 g, 5.48 mol, 2.0 eq) were added. The catalyst Pd(dppf)Cl$_2$ (30.07 g, 0.04 mol, 0.015 eq) was added under the protection of nitrogen. The external temperature was set at 110° C., and the mixture was stirred under the protection of nitrogen for 16.72 hours. LCMS and HPLC showed that the reaction was completed. The mixture was concentrated to remove the solvent. The residue was slurried with a mixture of ethyl acetate, n-heptane and water (600 ml:600 ml:600 ml) under stirring, and then filtered. The filter cake was washed once with 500 ml of water, and then dried to give the compound h (1501.41 g, crude product) as a black-brown solid.

LCMS (5-95AB): m/z: 332.2 [M+1].

$^1$H NMR (400 MHz, DMSO-d6): δ 8.12-8.15 (m, 2H), 8.00 (br s, 2H), 7.58-7.43 (m, 4H), 7.42-7.27 (m, 5H), 4.73 (s, 2H), 4.66 (s, 2H).

Step 5:

Hydrochloric acid (10.5 L) was added to compound h (1500.00 g, 4.53 mol, 1.0 eq). The resulting mixture was stirred at 40° C. for 29.13 hours, and LCMS and HPLC showed that the reaction was almost completed. The reaction solution was filtered, and the filter cake was dried. The pH of the filtration in ice water bath was adjusted to 7 to 8 with sodium hydroxide solid, and a solid was precipitated under stirring. The resulting mixture was filtered and the filter cake was dried. The filter cakes were combined to give the compound i (1160.00 g, crude product) as a yellow solid.

LCMS (5-95AB): m/z: 242.2 [M+1].

$^1$H NMR (400 MHz, DMSO-d6): δ 8.10-8.14 (m, 2H), 7.94 (br s, 2H), 7.54-7.39 (m, 4H), 5.60 (br s, 1H), 4.66 (s, 2H).

Step 6:

Compound i (400.90 g, 1.66 mol, 1.0 eq) was added to N,N-dimethylformamide (2 L) in a 3 L three-necked flask, to which N-iodosuccinimide (560.00 g, 2.49 mol, 1.5 eq) was then added. The resulting mixture was stirred at 10° C. for 44.47 hours, and LCMS and HPLC showed that the reaction was completed. The reaction solution was added to water (6 L), and a large amount of solid was precipitated under stirring. The resulting mixture was filtered and the filter cake was washed with water (1 L). The filter cake was dried to give the compound j (652.22 g, crude product) as a yellow-brown solid.

LCMS (5-95AB): m/z: 368.1 [M+1].

$^1$H NMR (400 MHz, DMSO-d6): δ 8.11 (br s, 2H), 7.61-7.56 (m, 2H), 7.51-7.43 (m, 3H), 5.63 (brs, 1H), 4.66 (s, 2H).

Step 7:

Compound j (250.00 g, 680.94 mmol, 1.0 eq) was dissolved in 1,4-dioxane (2.5 L) and water (0.5 L), and then compound c (254.98 g, 888.15 mmol, 1.2 eq) and potassium phosphate (289.08 g, 1.36 mol, 2 eq) were added sequentially. 1,1-Bis(di-tert-butylphosphino)ferrocene palladium dichloride (13.31 g, 20.42 mmol, 0.03 eq) was added under the protection of nitrogen. The resulting mixture was heated to 110° C., and reacted for 16 hours. Samples were sent for LCMS and HPLC analysis, which showed that the reaction was completed. The reaction solution was concentrated to dryness under reduced pressure, and the solid was extracted with ethyl acetate (2.0 L) and water (3.0 L). Each time ethyl acetate (2.0 L) was added for extraction, and the solid was extracted four times. The organic phases were combined, and then 5.0 L of n-heptane was added and stirred evenly. The solution of the compound was filtered with silica gel (3 Kg, 200 to 300 mesh). 20 L of washing agent (ethyl acetate: 15 L, n-heptane: 5 L) was prepared to wash the filter cake. The filtrates were combined and evaporated to dryness with a rotary evaporator. The resulting solid was added to 1.0 L of ethyl acetate, and heated to 75° C. to dissolve the solid completely. The temperature was kept constant, and n-heptane (3.0 L) was slowly added dropwise. A white solid was then precipitated. The resulting mixture was cooled to 20° C.

and filtered. The solid was added to 0.5 L of ethanol, and heated to 75° C. to dissolve the solid completely. The temperature was kept constant, and water (3.6 L) was slowly added dropwise. A white solid was then precipitated. The resulting mixture was cooled to 30° C. and filtered. The solid was added to 0.9 L of ethanol, and heated to 75° C. to dissolve the solid completely. The temperature was kept constant, and water (2.0 L) was slowly added dropwise. A white solid was then precipitated. The resulting mixture was cooled to 30° C. and then filtered. The solid was oven dried to give the crystal form A of compound 1 (150.09 g, yield: 55%).

LCMS (10-80AB): m/z: 401.2 [M+1].

$^1$H NMR (400 MHz, DMSO-d6) δ 8.29 (br s, 2H), 7.56 (s, 1H), 7.24-7.44 (m, 6H), 5.56 (t, J=6.0 Hz, 1H), 4.66 (d, J=6.0 Hz, 2H), 2.48 (3H, s).

Assay Example 1: Determination of Solubility of Crystal Form A of Compound 1

Multiple portions of about 2.0 mg of crystal form A of compound 1 were weighed in parallel and placed in glass vials. Various single solvents or mixed solvents listed in Table 2 were gradually added in small amount, and shaken constantly, while the dissolution of the compound was observed. The solubility of the compound was calculated based on the weight of the weighed compound and the volume of the correspondingly added solvent. The detailed results are shown in Table 2.

TABLE 2

Solubility results of the crystal form A of compound 1

| No. | Solvent | Solubility (mg/mL) |
| --- | --- | --- |
| 1 | Methanol | 47.5 < S < 95.0 |
| 2 | Ethanol | 28.8 < S < 38.3 |
| 3 | Isopropanol | 14.4 < S < 16.4 |
| 4 | N-butanol | 15.7 < S < 18.3 |
| 5 | Acetonitrile | 12.2 < S < 13.8 |
| 6 | Acetone | 33.3 < S < 50.0 |
| 7 | Methyl ethyl ketone | 36.7 < S < 55.0 |
| 8 | Ethyl acetate | 12.5 < S < 16.7 |
| 9 | Tetrahydrofuran | S > 105.0 |
| 10 | 1,4-Dioxane | 35.0 < S < 52.5 |
| 11 | Ethanol:Water (3:1) | 25.0 < S < 50.0 |
| 12 | Acetonitrile:Water (2:1) | 26.3 < S < 35.0 |

Note:
S stands for solubility.

Conclusion: The crystal form A of compound 1 has good solubility in the above solvents. Assay Example 2: In Vitro Activity Assay Calcium Flux Assay of the Human Adenosine $A_{2a}$ Receptor Cell Source:

The cell line stably expressing $A_{2a}$ was constructed by Shanghai WuXi AppTec, and the host cells were CHO cells.

Assay Kit:

Fluo-4 Direct kit (Invitrogen, Cat. No. F10471). The fluorescence detection reagent in the kit (which can specifically bind to calcium ions and cause an increase in the fluorescence signal) was incubated with the cells for an appropriate period of time, and the compounds were added to stimulate the cells to cause changes in the intracellular calcium flux, thereby causing changes in the fluorescence signal, which can reflect the strength of the agonistic or inhibitory activity of the compounds.

Cell Culture Medium:

F12+10% fetal bovine serum+geneticin 300 μg/ml+blasticidin 2 μg/ml

Compound Dilution Buffer:

Hanks balanced salt buffer (Invitrogen)+20 mM HEPES, prepared before each use

Agonist:

NECA (Sigma-E2387)

Reference Compound (Antagonist):

CGS-15943 (Sigma-C199)

Dilution of the Compounds:

The test compound was dissolved in DMSO to prepare a 10 mM stock solution. The test compound was diluted to 0.2 mM with DMSO, and the reference compound CGS-15943 was diluted to 0.015 mM with DMSO. Then the resulting dilutions were subjected to a 3-fold serial gradient dilution in ECHO, resulting in 10 concentration points. 900 nl of the resulting dilutions were transferred to the compound plate (Greiner-781280), and 30 μl of the compound dilution buffer was added. The final starting concentration of the test compound was 1 μM, and the final starting concentration of CGS-15943 was 0.075 μM.

Assay Method:

Cell Preparation:

The cryopreserved $A_{2A}$ cells were resuscitated and then resuspended in the culture medium to 1×10$^6$ cells/ml, and 20 μl/well of the suspension was seeded into a 384-well polylysine-coated cell plate (Greiner-781946). The cells were incubated overnight in a 5% $CO_2$, 37° C. incubator.

The cell plate prepared the day before was taken out of the incubator. 20 μl of 2× Fluo-4 Direct™ buffer was added to each well. The cell plate was incubated in a 5% $CO_2$, 37° C. incubator for 50 minutes, and then left at room temperature for 10 minutes.

Determination of EC80 of Agonist NECA:

Dilution of the agonist NECA: NECA was subjected to a 3-fold serial gradient dilution in Echo from an starting concentration of 0.15 mM, resulting in 10 concentration points. Then 900 nL of the resulting dilutions were transferred to the corresponding compound plate, and 30 μl of the compound dilution buffer was added to the corresponding compound plate. The final starting concentration was 750 nM.

FLIPR instrument software was run. According to the set program, 10 μl of the compound dilution buffer was added to the cell plate, and the fluorescence signal was read. Then 10 μl of a predetermined concentration of the agonist as a reference compound was added to the cell plate, and the fluorescence signal was read. After the reading, data was exported through the "Max-Min" and "Read 90 to Maximum allowed" methods in the software. EC80 of the $A_{2A}$ cell line was calculated, and the agonist with a concentration of 6×EC80 was prepared. The agonist as a reference compound with a concentration of 6×EC80 for the corresponding cells were prepared with the buffered salt solution, and added at 30 μl/well to the corresponding compound plate for use.

Determination of $IC_{50}$ of the Test Compound:

FLIPR instrument software was run. According to the set program, 10 μl of a predetermined concentration of the test compound and the reference compound were added to the cell plate, and the fluorescence signal was read. Again, 10 μl of the agonist as a reference compound with a concentration of 6×EC80 was added to the cell plate, and the fluorescence signal was read. For the agonist detection of the compound, data was exported through the "Max-Min" and "Read 1 to 90" methods in the software. For the antagonist detection of the compound, data was exported through the "Max-Min" and "Read 90 to Maximum allowed" methods in the software. The data was analyzed by GraphPad Prism 5.0, and the $IC_{50}$ value of the test compound was calculated.

TABLE 3

Result of in vitro screening assay of compound 1

| Compound No. | $IC_{50}$ value (nm) |
|---|---|
| Compound 1 | 0.65 |

Conclusion: As shown in Table 3, compound 1 exhibits excellent antagonistic activity against the adenosine $A_{2a}$ receptor.

Assay Example 3: Evaluation of Pharmacokinetics of the Compound

Object of the assay: to test the pharmacokinetics of the compound in female Balb/c mice in vivo Materials of the Assay:

Balb/c mice (female, 15 to 30 g, 7 to 9 weeks old, from Shanghai Lingchang Biotechnology Company)

Assay Procedures:

The pharmacokinetic profile of the compound after intravenous injection and oral administration in the rodents was tested by the standard protocol. In the assay, the candidate compound was prepared into a clear solution to be administered to the mice through a single intravenous injection and prepared into a homogeneous suspension to be administered to the mice through a single oral administration. The vehicle for the intravenous injection was 5% DMSO/95% 10% Cremophor EL, and the vehicle for the oral administration was 1% Tween 80, 9% PEG400, and 90% water. The whole blood sample was collected within 24 hours, and centrifuged at 3000 g at 4° C. for 15 minutes. The supernatant was separated to give the plasma sample, and 20 times volume of acetonitrile solution containing an internal standard was added to precipitate the proteins. The resulting mixture was centrifuged and the supernatant was taken out, to which an equal volume of water was added and centrifuged. The supernatant was taken out, and injected as a sample to quantitatively analyze the plasma drug concentration by LC-MS/MS analysis method. The pharmacokinetic parameters were calculated, such as peak concentration, peak time, clearance rate, half-life, area under the drug-time curve, bioavailability, etc.

Results:

TABLE 4

Pharmacokinetic assay results

| Test product (compound prepared in each example) | Clearance rate (mL/min/kg) | Half-life $T_{1/2}$ (h) | Concentration integral AUC (nM · hr) | Bioavailability F (%) |
|---|---|---|---|---|
| Compound 1 | 18 | 1.2 | 22005 | 95.2 |

Conclusion: Compound 1 shows excellent pharmacokinetic index in mice.

Assay Example 4: Study of Pharmacodynamics of Crystal Form a of Compound 1 In Vivo in CT-26 Model Materials of the Assay:

BALB/c nude mice (female, 7 weeks old, and weighing about 16 to 20 g) were kept in a breeding environment of SPF-class animal room, and in single ventilated cages (5 mice per cage). Bedding and water in all cages were disinfected before use. All the animals had free access to the standard certified commercial laboratory diet. A total of 80 mice were purchased from Shanghai Slack Laboratory Animal Co., Ltd. Anti-PD-1 antibody was purchased from BioXcell with the clone of RMP-14 and the product number of BP0146. 0.1 mL of 3×10⁵ CT26 cells were subcutaneously inoculated in the right back of each mouse, and the mice were randomly divided into groups for administration.

Assay Procedures:

CT26 cells were subcutaneously inoculated in the right back of each BALB/c nude mouse to test pharmacodynamics in vivo. In the assay, the test compound was administered orally every day for 22 consecutive days, and the anti-PD-1 antibody was administered once per week for three consecutive weeks. The volume of the tumor was measured twice a week with a two-dimensional caliper, and the volume was measured in cubic millimeter, which was calculated by the following formula: $V=0.5\ a\times b^2$, wherein a and b were the long and short diameters of the tumor, respectively. The anti-tumor efficacy was determined by dividing the average volume increase of the tumors of animals treated with the compound by the average volume increase of the tumors of the untreated animals. (BID means twice a day)

Results of the assay were shown in Table 5.

TABLE 5

| | Volume of tumor (mm³) | | | | | |
|---|---|---|---|---|---|---|
| Test compound | Day 10 | Day 13 | Day 15 | Day 18 | Day 20 | Day 22 |
| Blank group | 76 | 187 | 293 | 556 | 868 | 1249 |
| Anti-PD-1 (5 mg/Kg, QW) | 59 | 134 | 242 | 443 | 524 | 724 |
| Crystal form A of compound 1 (50 mg/Kg, BID) | 47 | 127 | 204 | 312 | 409 | 538 |
| Crystal form A of compound 1 + anti-PD-1 (50 mg/Kg, BID + 5 mg/Kg, QW) | 45 | 100 | 122 | 215 | 249 | 272 |

Conclusion:

The crystal form A of compound 1 (50 mg/Kg, BID) as a single drug has an anti-tumor effect. The combination of crystal form A of compound 1 (50 mg/Kg, BID) and anti-PD-1 (5 mg/Kg, QW) has a significant combined anti-tumor effect.

What is claimed is:

1. A crystal form A of (5-amino-8-(2-methyl-6-(trifluoromethyl)pyridin-4-yl)-7-phenyl-[1,2,4]triazolo[1,5-c]pyrimidin-2-yl)methanol (Compound 1) of the following formula:

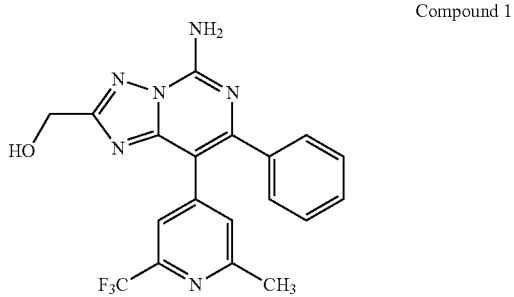 [SMILES: Cc1cc(-c2c(-c3ccccc3)nc(N)n3nc(CO)nc23)cc(C(F)(F)F)n1]

Compound 1 wherein the crystal form A is characterized by an X-ray powder diffraction pattern comprising characteristic diffraction peaks (° 2θ) at the following angles of 11.30°±0.2° 2θ, 16.90°±0.2° 2θ, and 22.52°±0.2° 2θ.

2. The crystal form A according to claim 1, wherein the crystal form A is further characterized by an X-ray powder diffraction pattern further comprising additional characteristic diffraction peaks (° 2θ) at the following angles of 8.08°±0.2° 2θ, 14.00°±0.2° 2θ, 18.30°±0.2° 2θ, 23.15°±0.2° 2θ, and 25.26°±0.2° 2θ.

3. The crystal form A according to claim 2, wherein the crystal form A is further characterized by an X-ray powder diffraction pattern as shown in FIG. 1.

4. The crystal form A according to claim 1, wherein the crystal form A is further characterized by a differential scanning calorimetry curve having a starting point of the endothermic peak at 198.61° C.±2° C.

Figure 2:
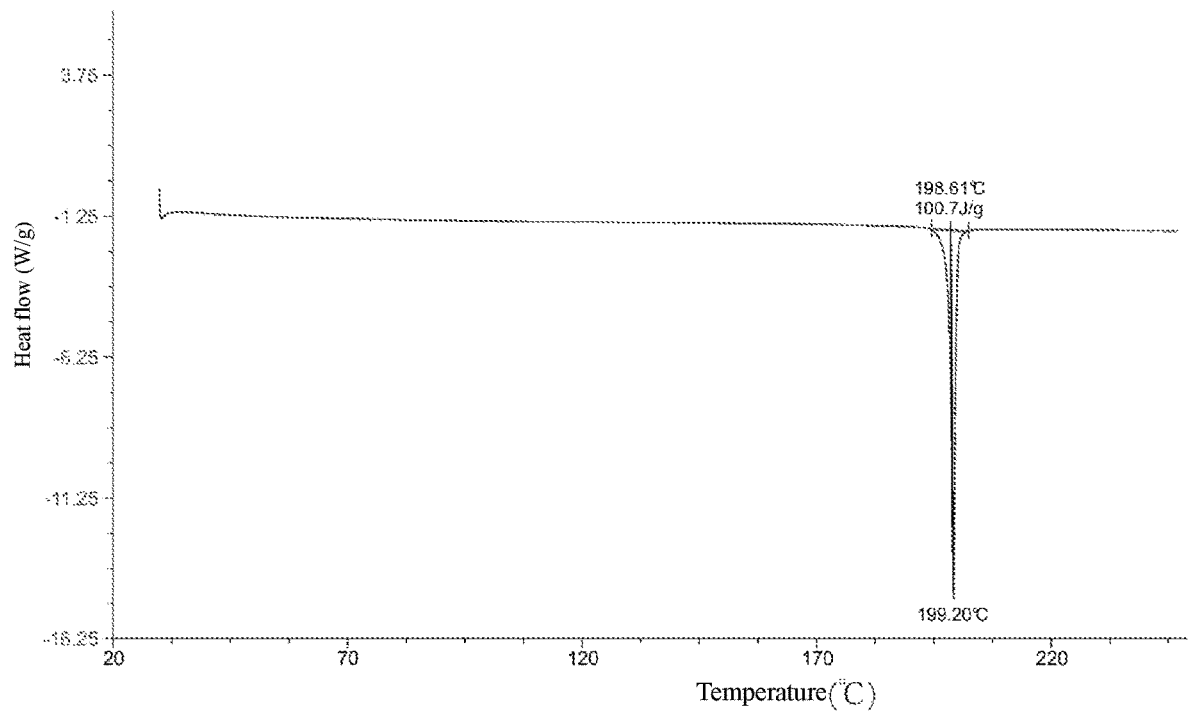
FIG. 2 is the DSC curve of the crystal form A of compound 1.

5. The crystal form A according to claim 4, wherein the crystal form A is further characterized by a differential scanning calorimetry curve as shown in FIG. 2.

6. The crystal form A according to claim 1, wherein the crystal form A is further characterized by a thermogravimetric analysis curve having a weight loss in the range of 0.0% to 0.4423% at 199.80° C.±3° C.

7. The crystal form A according to claim 4, wherein the crystal form A is further characterized by a thermogravimetric analysis curve having a weight loss in the range of 0.0% to 0.4423% at 199.80° C.±3° C.

Figure 3:
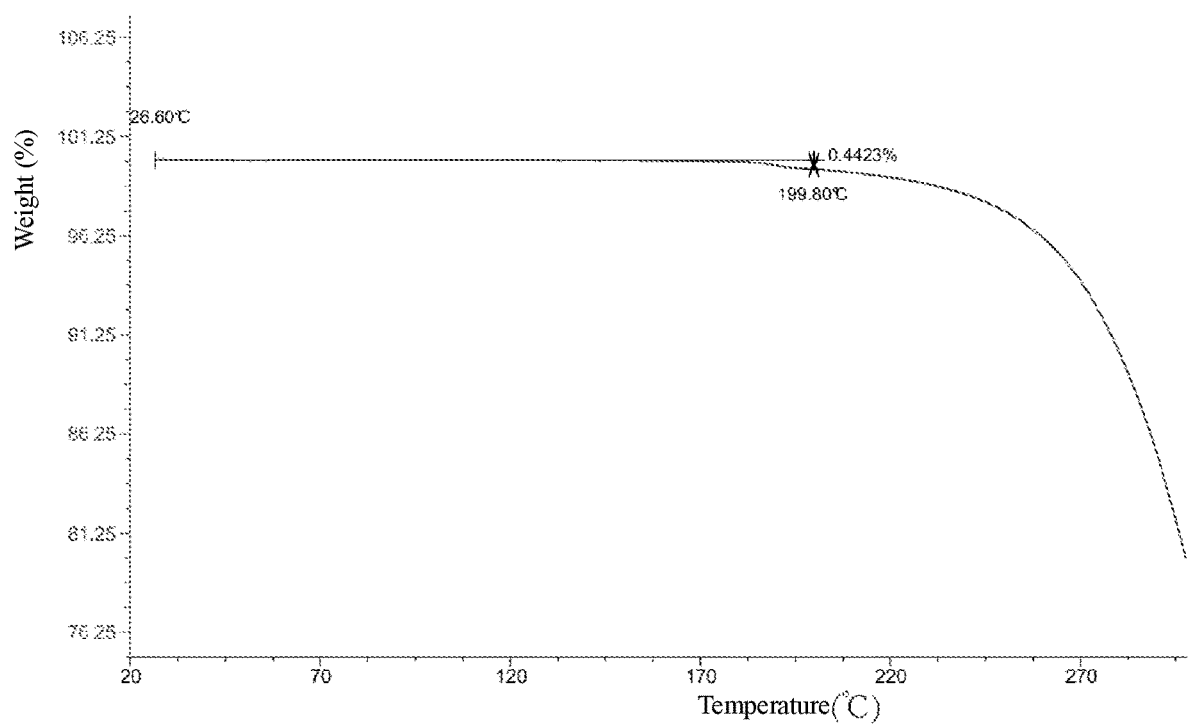
FIG. 3 is the TGA curve of the crystal form A of compound 1.

8. The crystal form A according to claim 6, wherein the crystal form A is further characterized by a thermogravimetric analysis curve as shown in FIG. 3.

9. The crystal form A according to claim 7, wherein the crystal form A is further characterized by a thermogravimetric analysis curve as shown in FIG. 3.

10. A method for inhibiting the activity of an adenosine $A_{2A}$ receptor in a subject in need thereof, wherein the method comprises administering to the subject the crystal form A according to claim 1.

11. The method according to claim 10, wherein the subject has a disease related to the adenosine $A_{2A}$ receptor, and wherein the disease related to the adenosine $A_{2A}$ receptor is colon cancer or rectal cancer.

12. The method according to claim 11, wherein the disease related to the adenosine $A_{2A}$ receptor is colorectal cancer.

* * * * *